United States Patent [19]
Pinney

[11] Patent Number: 5,886,025
[45] Date of Patent: Mar. 23, 1999

[54] ANTI-MITOTIC AGENTS WHICH INHIBIT TUBULIN POLYMERIZATION

[75] Inventor: Kevin G. Pinney, Hewitt, Tex.

[73] Assignee: Baylor University, Waco, Tex.

[21] Appl. No.: 813,018

[22] Filed: Mar. 6, 1997

[51] Int. Cl.[6] .................. A61K 31/38; C07D 333/54
[52] U.S. Cl. .................. 514/443; 549/51; 549/57; 549/58
[58] Field of Search .................. 549/57, 58, 51; 514/443

[56] References Cited

U.S. PATENT DOCUMENTS

| | | | |
|---|---|---|---|
| 4,133,814 | 1/1979 | Jones et al. | 546/202 |
| 4,380,635 | 4/1983 | Peters | 546/202 |
| 4,656,187 | 4/1987 | Black et al. | 514/442 |
| 5,532,382 | 7/1996 | Carlson et al. | 549/57 |
| 5,596,106 | 1/1997 | Cullinan et al. | 549/57 |

FOREIGN PATENT DOCUMENTS

| | | |
|---|---|---|
| 0 729 755 A2 | 9/1996 | European Pat. Off. . |
| 0 729 755 A3 | 9/1996 | European Pat. Off. . |
| WO 95/10513 | 4/1995 | WIPO . |

OTHER PUBLICATIONS

Bai, Schwartz, Kepler, Pettit and Hamel, "Characterization of the Interaction of Cryptophycin 1 with Tubulin: Binding in the Vinca Domain, Competitive Inhibition of Dolastatin 10 and an Unusual Aggregation Reaction," Cancer Res., 56:4398–4406, 1996.

Boger and Curran, "Synthesis of the lower subunit of rhizoxin," J. Org. Chem., 57:2235, 1992.

Chan and Fong, "Inhibition of Leishmanias but not host macrophages by the antitubulin herbicide Trifluralin," Science, 249:924–926, 1990.

Chavan, Richardson, Kim, Haley, Watt, Forskolin, "Photoaffinity probes for the evaluation of tubulin binding sites," Bioconjugate Chem., 4:268, 1993.

Cushman, Nagarathnam, Gopal, Chakraborti, Lin, Hamel, "Synthesis and evaluation of stilbene and dihydrostilbene derivatives as potential anticancer agents that inhibit tubulin polymerization," J. Med. Chem., 34:2579, 1991.

D'Amato, Lin, Flynn, Folkman, Hamel, "2–methoxyesteradiol, an endogenous mammalian metabolite, inhibits tubulin polymeriation by interacting at the colchicine site," Proc. Natl. Acad. Sci. USA, 91:3964, 1994.

Floyd, Barnes, Williams, "Photoaffinity labeling of tubulin with (2–nitro–4–azidophenyl)deacetylcolchicine: direct evidence for two colchicine binding sites," Biochemistry, 28:8515, 1989.

Gerwick, Proteau, Nagle, Hamel, Blokhin, Slate, "Structure of curacin A, a novel antimitotic, antiproliferative, and brine shrimp toxic natural product from the marine cyanobacterium Lyngbya majuscula," J. Org. Chem., 59:1243,1994.

Hamel and Lin, "Separation of active tubulin and microtubule–associated proteins by ultracentrifugation and isolation of a component causing the formation of microtubule bundles," Biochemistry, 23:4173, 1984.

Jiang, Hesson, Dusak, Dexter, Kang, Hamel, "Synthesis and biological evaluation of 2–styrylquinazoline–4(3H)–ones, a new class of antimitotic anticancer agents which inhibit tubulin polymerization," J. Med. Chem., 33:1721, 1990.

Jones, Jevnikar, Pike, Peters, Black, Thompson, Falcone, Clemens, "Antiestrogens. 2. Structure–activity studies in a series of 3–aroyl–2–arylbenzo[b]thiophene derivatives leading to [6–hydroxy–2–(4–hydroxyphenyl)benzo[b]thien–3–yl][4–[2–(1–piperdinyl)ethoxy]–phenyl]methanone hydrochloride (LY156758), a remarkably effective estrogen antagonist with only minimal intrinsic estrogenicity," J. Med. Chem., 27:1057, 1984.

Jones, Suarez, Massey, Black, Tinsley, "Synthesis and anti-estrogenic activity of [3,4–dihydro–2–(4–methoxyphenyl)–1–naphthalenyl][4–[2–(1–pyrrolidinyl)ethoxy]–phenyl]methanone, methanesulfonic acid salt," J. Med. Chem., 22(8):962, 1979.

Kang, Getohun, Muzaffar, Brossi, Hamel "N–acetylcolchinol O–methyl ether and triocolchicine, potent analogs of colchicine modified in the C ring," J. Biol. Chem., 265, 10255, 1990.

Kobayashi, Nakada, Ohno, "Synthetic study on an antitumor antibiotic rhizoxin by using an enzymatic process on prochiral beta–substituted glutarates," Pure Appl. Chem., 64(8):1121–1124, 1992.

Kobayashi, Nakada, Ohno, "Synthetic study on an antitumor antibiotic rhizoxin by using an enzymatic process on prochiral beta–substituted glutarates," Indian J. Chem., 32B:159–162, 1993.

Kym, Anstead, Pinney, Wilson, Katzenellenbogen, "Molecular structures, conformational analysis, and preferential modes of binding of 3–aroyl–2–arylbenzol[b] thiophene estrogen receptor ligands: LY117018 and aryl azide photoaffinity labeling analogs," J. Med. Chem., 36:3910, 1993.

Lavielle, Havtefaye, Schaeffer, Boutin, Cudennec, Pierre, "New α–amino phosphonic acid derivatives of vinblastine: chemistry and antitumor activity," J. Med. Chem., 34:1998, 1991.

Lin, Ho, Pettit, Hamel, "Antimitotic natural products combretastatin A–4 and combretastatin A–2: studies on the mechanism of their inhibition of the binding of colchicine to tubulin," Biochemistry, 28:6984, 1989.

Maldonado et al., "Experimental Chemotherapy with Combinations of Ergosterol Biosynthesis Inhibitors in Murine Models of Chagas' Disease," Antimicrobial Agents and Chemotherapy, 37(6):1353–1359, 1993.

(List continued on next page.)

Primary Examiner—Jane Fan
Attorney, Agent, or Firm—Arnold White & Durkee

[57] ABSTRACT

Methoxy and ethoxy substituted 3-aroyl-2-arylbenzo[b] thiophenes and benzo[b]thiophene analogues are described for use in inhibiting tubulin polymerization. The compounds' use for treating tumor cells is also described.

11 Claims, 2 Drawing Sheets

OTHER PUBLICATIONS

Mullica, Pinney, Dingeman, Bounds, Sappenfield, "X–ray structures of two methoxybenzol[b]thiophenes," *J. Chem. Cryst.*, 1996, [Submitted].

Muzaffar, Brossi, Lin, Hamel, "Antitubulin effects of derivatives of 3–demethylthiocolchicine, methylthio ethers of natural colchicinoids, and thioketones derived from thiocolchicine. Comparison with colchicinoids," *J. Med. Chem.*, 33:567, 1990.

Nakada, Kobayashi, Iwasaki, Ohno, "The first total synthesis of the antitumor macrolide rhizoxin: synthesis of the key building blocks," *Tetrahedron Lett.*, 34:1035, 1993.

Nakada, Kobayashi, Iwasaki, Ohno, "The first total synthesis of the antitumor macrolide rhizoxin," *Tetrahedron Lett.*, 34:1039, 1993.

Owellen, Hartke, Kickerson, Hains, "Inhibition of tubulin–microtubule polymerization by drugs of the vinca alkaloid class," *Cancer Res.*, 36:1499, 1976.

Parness and Horwitz, "Taxol binds to polymerized tubulin in vitro," *J. Cell Biol.*, 91:479, 1981.

Pettit, Cragg, Herald, Schmidt, Lohavanijaya, "Isolation and structure of combretastatin," *Can. J. Chem.*, 60:1374, 1982.

Pettit et al., "Isolation and X–Ray Crystal Structure of Raoemic Xestospongin D From the Singapore Marine Sponge Niphates SP[1]," Bioorganic & Medicinal Chenistry Letters, 6(12):1313–1318, 1996.

Pettit, Singh, Cragg, "Synthesis of natural (–)–combretastatin," *J. Org. Chem.*, 50:3404, 1985.

Pinney and Katzenellenbogen, "Synthesis of tetrafluor–substituted aryl azide and its protio analogue as photoaffinity labeling reagents for the estrogen receptor," *J. Org. Chem.*, 56:3125, 1991.

Pinney, Carlson, Katzenellenbogen, Katzenellenbogen, "Efficient and selective photoaffinity labeling of the estrogen receptor using two nonsteroidal ligands that embody aryl azide or tetrafluoroaryl azide photoreactive functions," *Biochemistry*, 30:2421, 1991.

Rao, Bhanu, Sharma, "Studies directed towards the total synthesis of rhizoxin: stereoselective synthesis of C–12 to C–18 segment," *Tetrahedron Lett.* 34:707, 1993.

Rao, Krauss, Heerding, Swindell, Ringel, Orr, Horwitz, "3'–(p–azidobenzamido)taxol photolabels the N–terminal 31 amino acids of B–tubulin," *J. Biol. Chem.*, 269:3132, 1994.

Rao, Sharma, Bhanu, "Radical mediated enantioselective construction of C–1 to C–9 segment of shizoxin," *Tetrahedron Lett.* 33:3907, 1992.

Safa, Hamel, Felsted, "Photoaffinity labeling of tubulin subunits with a photoactive analog of vinblastine," *Biochemistry*, 26:97, 1987.

Sawada, Hashimoto, Li, Kobayashi, Iwasaki, Fluorescent and photoaffinity labeling derviatives of rhizoxin, *Biochem. Biophys. Res. Commun.*, 178:558, 1991.

Sawada, Kato, Kobayashi, Hashimoto, Watanabe, Sugiyama, Iwasaki, "A fluorescent probe and a photoaffinity labeling reagent to study the binding site of maytansine and rhizoxin on tubulin," *Bioconjugate Chem.*, 4:284, 1993.

Schiff, Fant, Horwitz, Promotion of microtubule assembly in vitro by taxol, *Nature*, 277:665, 1979.

Shirai, Tokuda, Koiso, Iwasaki, "Synthesis and anti–tubulin activity of aza–combretastatins," *Biomedical Chem. Lett.*, 699, 1994.

Staretz and Hastie, "Synthesis, photochemical reactions, and tubulin binding of novel photoaffinity labeling derivatives of colchicine," *J. Org. Chem.*, 58:1589, 1993.

Swindell, Heerding, Krauss, Horowitz, Rao, Ringel, "Characterization of two taxol photoaffinity analogues bearing azide and benzophenone–related photoreactive substituents in the A–ring side chain," *J. Med. Chem.*, 37:1446–1449, 1994.

Swindell, Krauss, Horwitz, Ringel, "Biologically active taxol analogs with deleted A–ring side chain substituents and variable C–2' configurations," *J. Med. Chem.*, 34:1176–1184, 1991.

Williams, Mumford, Williams, Floyd, Aivaliotis, Martinez, Robinson, Barnes, "A photoaffinity derivative of colchicine: 6–(4'–axido–2'–nitrophenylamino)hexanoyldeacetylcolchicine. photolabeling and location of the colchicine–binding site on the alpha–subunit of tubulin," *J. Biol. Chem.*, 260:13794, 1985.

Wolff, Knipling, Cahnmann, Palumbo, "Direct photoaffinity labeling of tubulin with colchicine," *Proc. Natl. Acad. Sci. USA*, 88:2820, 1991.

World Health Organization, Tropical disease research progress, 1991–1992.

De Castro, "The challenge of Chagas' disease chemotherapy: an update of drugs assayed against *Trypanasoma cruzi*," *Acta. Trop.*, 53:83–98, 1993.

Marr and Docamp, "Chemotherapy for Chagas' disease: A perspective of current therapy and considerations for future research," *Rev. Infect. Dis.*, 8:884–903, 1986.

Prata, "Chagas' Disease," *Infect. Dis. Clin. North. Amer.*, 8:61–76, 1994.

Rao, Horwitz, Ringel, "Direct photoaffinity labeling of tubulin with taxol," *J. Natl. Cancer Inst.*, 84:785, 1992.

Sawada, Kobayashi, Hashimoto, Iwasaki, "Identification of the fragment photoaffinity–labeled with azidodansylrhizoxin as Met–363—Lys–379 on beta–tubulin," *Biochem Pharmacol.*, 45:1387, 1993.

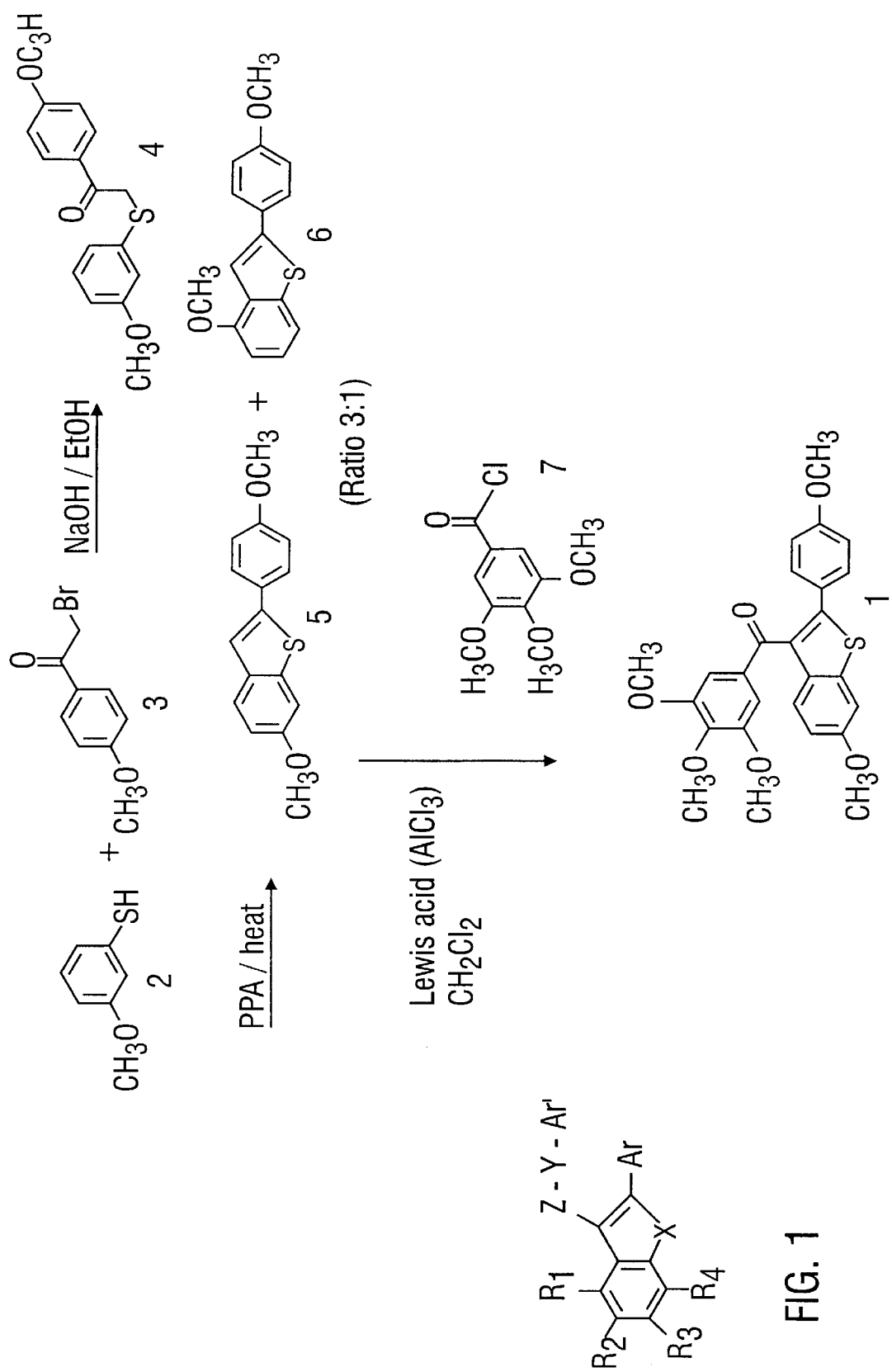

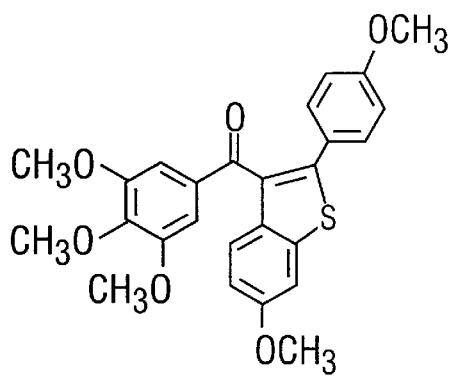 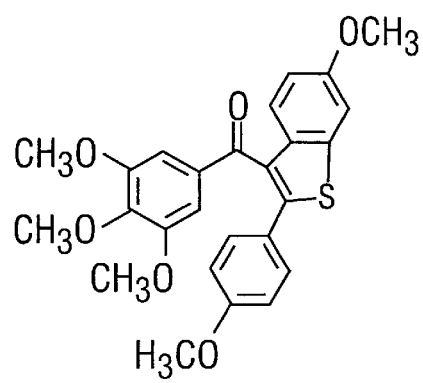
FIG. 2A  FIG. 2B
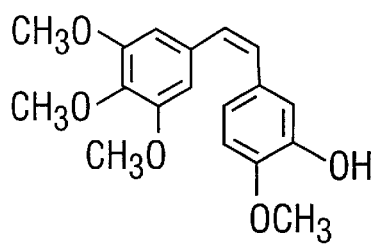
FIG. 2C
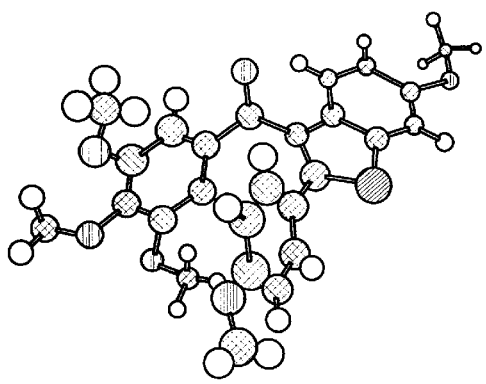 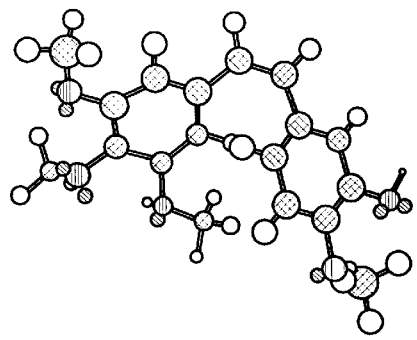
FIG. 3A  FIG. 3B

ANTI-MITOTIC AGENTS WHICH INHIBIT TUBULIN POLYMERIZATION

BACKGROUND OF THE INVENTION

1. Field of the Invention

The present invention relates generally to the field of tubulin polymerization inhibitors. More particularly, it concerns the use of 3-aroyl-2-aryl-benzo[b]thiophenes and analogues thereof as anti-tumor agents.

2. Description of Related Art

An aggressive chemotherapeutic strategy toward the treatment and maintenance of solid-tumor cancers continues to rely on the development of architecturally new and biologically more potent anti-tumor, anti-mitotic agents. A variety of clinically-promising compounds which demonstrate potent cytotoxic and anti-tumor activity are known to effect their primary mode of action through an efficient inhibition of tubulin polymerization (Gerwick et al.). This class of compounds undergoes an initial binding interaction to the ubiquitous protein tubulin which in turn arrests the ability of tubulin to polymerize into microtubules which are essential components for cell maintenance and cell division (Owellen et al.).

Currently the most recognized and clinically useful tubulin polymerization inhibitors for the treatment of cancer are vinblastine and vincristine (Lavielle, et al.). Additionally, the natural products rhizoxin (Nakada, et al., 1993a and 1993b; Boger et al; Rao et al., 1992 and 1993; Kobayashi et al., 1992 and 1993) combretastin A-4 and A-2 (Lin et al.; Pettit, et al., 1982, 1985, and 1987) and taxol (Kingston et al; Schiff et al; Swindell, et a, 1991; Parness, et al.) as well as certain synthetic analogues including the 2-styrylquinazolin-4(3H)-ones (SQO) (Jiang et al.) and highly oxygenated derivatives of cis- and trans-stilbene (Cushman et al.) and dihydrostilbene are all known to mediate their cytotoxic activity through a binding interaction with tubulin. The exact nature of this interaction remains unknown and most likely varies somewhat between the series of compounds.

Tubulin is a heterodimer of the globular α and β tubulin subunits. A number of photoaffinity labeling reagents for tubulin have been developed and evaluated (Rao et al., 1992 and 1994; Chavan et al.; Sawada et al., 1991, 1993a and 1993b; Staretz et al.; Hahn et al; Wolff et al.; Floyd et al; Safa et al.; Williams et al.). These reagents have identified three distinct small molecule binding sites on tubulin: the colchicine site, the vinblastine site and the maytansine/rhizoxin site. Additionally, a first generation rhizoxin-based photoaffinity labeling reagent has suggested binding to the Met-363-Lys-379 site on β-tubulin (Sawada et al., 1993a), and a taxol-based reagent has been found to label the N-terminal 31 amino acid residues of β-tubulin (Swindell et al, 1991 and 1994; Rao et al., 1994). Taxol itself is known to bind to polymerized microtubules, but not at distinct sites on the monomer subunits of tubulin (Kingston et al.; Schiff et al.; Swindell et al., 1991; Parness et al.).

Recent studies (Shirai et al., D'Amato et al.) have suggested that compounds which are estrogenic in nature and also contain a methoxy aryl functionality show increased binding at the colchicine binding site of tubulin. These compounds may be estrogens or antiestrogens which bind to the estrogen receptor. One compound of this type which has already been shown to be a viable inhibitor of tubulin polymerization is 2-methoxyestradiol (D'Amato et al). As a steroid, however, the use of 2-methoxyestradiol as an anti-cancer agent may lead to unwanted side effects.

Even before the discovery that estrogenic compounds were inhibitors of tubulin polymerization, antiestrogens were developed to treat hormone-dependent cancers and a number of nonsteroidal agents were developed. Tamoxifen, for instance, has been widely used to treat estrogen-dependent metastatic mammary carcinoma (Mouridsen, et al.). The structure of trioxifene mesylate, a tetralin based compound which exhibits anti-tumor effects at the same or higher level as tamoxifen (Jones et al., 1979), includes a ketone moiety as part of its triarylethylene core, thereby overcoming the isomerization tendencies of the ethylene double bond of this class of compounds, assuring the stability of the molecule's three-dimensional structure. Unfortunately, despite their antiestrogen properties, tamoxifen and the related triarylethylene derivatives retain some intrinsic estrogen agonist properties, reducing their ability to fully inhibit biological responses to exogenous or endogenous estrogens (Jones et al., 1984).

The benzo[b]thiophenes are another example of a class of compounds which often exhibit very high affinity for the estrogen receptor (Kym et al.; Pinney et al., 1991a and 1991b; WO 95/10513). The 2,3-diaryl substituted benzo[b] thiophenes greatly resemble the triarylethylene-based core structure of tamoxifen. The estrogenicity of the triarylethylene compounds has been shown to be substantially overcome in 3-aroyl-2-arylbenzo[b]thiophene compounds substituted at the 3-aroyl group with basic amine moieties (Jones et al., 1984). A prime example of this type of compound is LY117018 (U.S. Pat. No. 4,656,187). 3-aroyl-2-arylbenzo[b]thiophenes have also been found to be useful antifertility agents (U.S. Pat. No. 4,133,814) and as inhibitors for 5-lipoxygenase (U.S. Pat. No. 5,532,382).

SUMMARY OF THE INVENTION

The present invention provides benzo[b]thiophene-based inhibitors of tubulin polymerization, thereby providing novel anti-tumor compounds of increased cytotoxicity and fewer side effects. This is accomplished through the introduction of small alkoxy aryl substituents to the estrogenic benzo[b]thiophene skeleton or the skeleton of compounds similar to benzo[b]thiophene, such as indene, benzofuran, and indole. The tubulin polymerization inhibitors of this invention are illustrated by the structure:

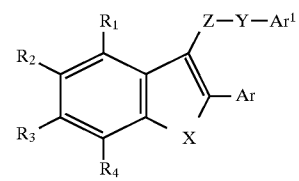

wherein

X is S, O, NH, or $CH_2$, $R_1$–$R_4$ are independently chosen from the group including H, OH and $C_1$–$C_5$ alkoxy, Z is C=O, $CH_2$, $C_2H_2$, CHOH, or $CHOCH_3$, Y is a covalent bond, $CH_2$, or $CH_2CH_2$ Ar and Ar' are aryl moieties, chosen from the group consisting of phenyl and napthyl, wherein each aryl group is further substituted with at least one $C_1$–$C_5$ alkoxy group.

Preferably, the tubulin polymerization inhibitors of this invention will be of the above formula wherein X is S. The most preferred R group substitution pattern will be wherein $R_3$ is $OCH_3$ and $R_1$, $R_2$ and $R_4$ are H. Z will preferably be C=O, Y will preferably be a covalent bond, and Ar will preferably be 4-methoxyphenyl. The most preferred Ar' groups will be singly and multiply substituted phenyl groups containing para ethoxy or methoxy substituents. The most preferred tubulin polymerization inhibitor of this invention is 3-(3',4',5'-trimethoxybenzoyl)-2-(4'-methoxyphenyl)-6-methoxybenzo[b]-thiophene.

The term "$C_1$-$C_5$ alkoxy" as used herein contemplates both straight chain and branched chain alkyl radicals and therefore defines groups such as, for example, methoxy, ethoxy, n-propoxy, isopropoxy, n-butyloxy, isobutyloxy, tert-butyloxy, sec-butyloxy, pentyloxy, isopentyloxy, t-pentyloxy, neopentyloxy, and the like. The preferred alkoxy groups are methoxy and ethoxy.

The novel compounds of this invention are of the structure:

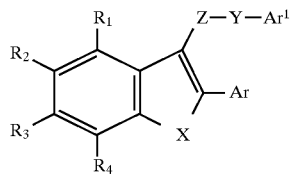

wherein
X is S, O, NH, or $CH_2$,
$R_1$–$R_4$ are independently chosen from the group including H, OH and $C_1$–$C_5$ alkoxy,
Z is C=O, $CH_2$, $C_2H_2$, CHOH, or $CHOCH_3$,
Y is a covalent bond, $CH_2$, or $CH_2CH_2$,
Ar and Ar' are aryl moieties, chosen from the group containing phenyl and napthyl, each aryl group substituted with at least one $C_1$–$C_5$ alkoxy group; wherein when Ar' is 3,4,5-trimethoxyphenyl or 4-methoxyphenyl, X is S, Z is C=O, Y is a covalent bond, $R_3$ is $OCH_3$, $R_1$, $R_2$, and $R_4$ are H, and Ar is a phenyl group that contains at least one methoxy substituent, then Ar must be substituted with a total of at least two alkoxy groups.

The preferred novel compounds of this invention will be those wherein X is S, Z is C=O, $R_3$ is methoxy and Ar is 4-methoxyphenyl. The preferred novel compounds of this invention include:

3-(2',3'-dimethoxybenzoyl)-2-(4'-methoxyphenyl)-6-methoxybenzo[b]thiophene, 3-(3',5'-dimethoxybenzoyl)-2-(4'-methoxyphenyl)-6-methoxybenzo[b]thiophene, 3-(3',4'-dimethoxybenzoyl)-2-(4'-methoxyphenyl)-6-methoxybenzo[b]thiophene, 3-(4'-ethoxybenzoyl)-2-(4'-methoxyphenyl)-6-methoxybenzo[b]thiophene, 3-(3',4',5'-triethoxybenzoyl)-2-(4'-methoxyphenyl)-6-methoxybenzo[b]-thiophene, and 3-[3'-(3",4",5"-trimethoxyphenyl)propanoyl]-2-(4'-methoxyphenyl)-6-methoxybenzo[b]thiophene.

The most preferred novel compounds of this invention will be those wherein X is S, Z is C=O, Ar is 4-methoxyphenyl, $R_3$ is methoxy, and Ar' is a phenyl group substituted with an alkoxy group at the para position. The most preferred novel compounds of this invention include:

3-(3',4'-dimethoxybenzoyl)-2-(4'-methoxyphenyl)-6-methoxybenzo[b]thiophene, 3-(4'-ethoxybenzoyl)-2-(4'-methoxyphenyl)-6-methoxybenzo[b]thiophene, 3-(3',4',5'-triethoxybenzoyl)-2-(4'-methoxyphenyl)-6-methoxybenzo[b]thiophene, and 3-[3'-(3",4",5"-trimethoxyphenyl)propanoyl]-2-(4'-methoxyphenyl)-6-methoxybenzo[b]thiophene.

As a preferred embodiment of the invention, the tubulin polymerization inhibitors will be used as part of pharmacologically active compositions for treating leukemias, melanomas, and colon, lung, ovarian, CNS, and renal cancers, as well as other cancers. In the most preferred embodiment of this aspect of the invention, the tubulin polymerization inhibitors will be used to treat colon cancers.

As a further preferred embodiment, the tubulin polymerization inhibitors of this invention may be used to treat any disease for which tubulin polymerization plays a crucial role. In addition to anti-tumor activity, caused by lack of mitosis in cells in which tubulin polymerization is absent, the tubulin polymerization inhibitors of this invention would also be useful in treating diseases caused by flagellated parasites, for whom tubulin polymerization is crucial to movement. In particular, the tubulin polymerization inhibitors of this invention will be useful in treating Chagas' disease or diseases caused by the parasite *Leishmania*.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 shows the general structure of the tubulin polymerization inhibitor compounds.

FIG. 2 shows the pseudo-cis (FIG. 2A) and pseudo-trans (FIG. 2B) orientations of 3-aroyl-benzo[b]thiophene compounds and the structure of Combretastatin A-4 (FIG. 2C).

FIG. 3 shows the X-ray crystal structure of 3-(3',4',5'-trimethoxybenzoyl)-2-(4'-methoxyphenyl)-6-methoxybenzo[b]thiophene (FIG. 3A) and the energy minimized (MM2) structure of Combretastatin A-4 (FIG. 3B).

FIG. 4 shows a general scheme for the synthesis of the 3-aroyl-2-phenybenzo[b]thiophene compounds.

DESCRIPTION OF ILLUSTRATIVE EMBODIMENTS

The present invention arises from the inventors' discovery that 3-(3'4'5'-trimethoxybenzoyl)-2-(4'-methoxyphenyl)-6-methoxybenzo[b]thiophene inhibits tubulin polymerization to nearly the same extent as Combretastatin A-4, one of the most potent tubulin polymerization inhibitors known. The tubulin polymerization $IC_{50}$ of the methoxyaroyl-substituted benzo[b]thiophene was 1.5–2.5 $\mu$M while that of Combretastatin A-4 was 0.75 $\mu$M. 3-(3'4'5'-trimethoxybenzoyl)-2-(4'-methoxyphenyl)-6-methoxybenzo[b]thiophene also showed significant cell growth inhibitory activity against a number of tumor cell lines. The compound was particularly effective against the colon KM20L2 cell line, exhibiting a $GI_{50}$ of $4.9 \times 10^{-2}$ $\mu$g/ml.

The molecular structure of the tubulin polymerization inhibitors of the present invention are based on the structure of benzo[b]thiophene and the similar structures of indole, benzofuran and indene (FIG. 1). The six-membered ring of these fused systems is substituted by one or more hydroxy or alkoxy groups, in any substitution pattern. C-2 of the benzo[b]thiophene, benzofuran or indole or C-3 of the indene is substituted with an aromatic moiety, preferably phenyl. This aromatic substituent will also contain one or more alkoxy substituents. Although it is unlikely that this group will interact at the colchicine binding site of tubulin, elaboration of the molecules at this site may provide interactions with other small molecule binding sites on tubulin.

C-3 of the benzo[b]thiophene, indole, or benzofuran and C-2 of the indene is also substituted with an alkoxy-substituted aryl moiety, and will contain a linker group connecting the parent benzo[b]thiophene, benzofuran, indole, or indene structure and the aromatic substituent. The linker group is of between one and three carbons, and may or may not contain a carbonyl functionality or another oxygen-containing group, such as hydroxy or methoxy. Possible linker groups include C=O, $CH_2$, $C_2H_2$, $C_2H_4$, $C_3H_6$, CHOH, $CHOCH_3$, C(=O)$CH_2$, CH(O$CH_3$)$CH_2$, CH(OH)$CH_2$, C(=O)$CH_2CH_2$, C(O$CH_3$)$CH_2CH_2$, and C(OH)$CH_2CH_2$.

The design of this new class of benzo[b]thiophene-based molecules takes advantage of the known estrogenicity of the benzo[b]thiophenes (Jones et al, 1984) and combines this trait with alkoxy substitution of the aryl rings, a factor recently discovered to be important in tubulin binding (Shirai, et al, D'Amato et al.) The 3-aroyl substituent of many of these new compounds is particularly useful because the carbonyl moiety, by forcing the adjoining atoms into or nearly into planarity, serves to reduce the number of three-dimensional configurations available to the substituted benzothiophene. Recent studies have shown that less flexible ligands, although they may bind to fewer molecules, generally have higher binding affinities. More flexible molecules, on the other hand, are less discriminatory in finding a binding partner, but usually bind with lower affinity (Eaton et al.).

The most likely configurations for the 3-aroylbenzo[b]thiophenes is either the pseudo-cis configuration (FIG. 2A) or the pseudo-trans configuration (FIG. 2B). It is well know that the cis or Z form of the stilbenoid Combretastatin A-4 (FIG. 2C) has a much higher binding affinity for tubulin as compared to its trans or E counterpart (Cushman et al.). As shown in FIG. 2, both the cis and trans configurations of the aroyl benzo[b]thiophenes retain a great deal of structural overlap with the cis conformation of Combretastatin A-4. Recently, the X-ray crystal structures of 3-(3',4',5'-trimethoxybenzoyl)-2-(4'-methoxyphenyl)-6-methoxybenzo[b]thiophene and other 3-aroyl-2-phenylbenzo[b]thiophenes were solved and show that the preferred conformation of the 3-aroylbenzo[b]thiophene compounds is indeed the pseudo-cis configuration (Mullica et al.). The X-ray crystal structure of 3-(3',4',5'-trimethoxybenzoyl)-2-(4'-methoxyphenyl)-6-methoxybenzo[b]thiophene and the computationally minimized (MM2) structure of Combretastatin A-4 are shown for comparison in FIG. 3.

A typical synthesis of the benzo[b]thiophene compounds is shown in FIG. 4 for 3-(3',4',5'-trimethoxybenzoyl)-2-(4'-methoxyphenyl)-6-methoxybenzo[b]thiophene 1. Intermediate 5, 6-methoxy-2-(4'-methoxyphenyl)-benzo[b]thiophene, was prepared from 3-methoxybenzene thiol 2 and bromoacetotophenone 3 according to the method of Kost et al. The polyphosphoric acid (PPA) catalyzed cyclization of the substituted thiol 4 produced regioisomers 5 and 6 in a 3:1 ratio separable due to differences in the molecules' solubility in acetone. The use of other thiols and acyl halides can allow for alternative substitution patterns on the benzene ring of the benzo[b]thiophene and the C-2 substituent aryl group. Alternatively, phenols or anilines may be used is place of the thiol to produce benzofurans or indoles. Friedel-Crafts aroylation of 5 results in functionalization at C-3 of the benzo[b]thiophene skeleton, giving the 3-aroyl-2-phenylbenzo[b]thiophene 1. By a similar scheme, Friedel-Crafts alkylation of 6-methoxy-2-(4'-methoxyphenyl)benzo[b]thiophene provides a route to the benzyl and phenylethyl substituted benzo[b]thiophenes, while reduction of the aroyl carbonyl can lead to the hydroxybenzyl compounds. Suitable reduction agents include lithium aluminum hydride and sodium borohydride. The hydroxy compounds can be further elaborated with the addition of alkoxy substituents through a variety of nucleophilic substitution reactions. For example, deprotonation of the benzylic alcohol formed from reduction of compound 1, followed by reaction with an alkyl halide could be used to form a benzylic ether. In addition, dehydration of a CH(OH)$CH_2$ or a CH(OH)$CH_2CH_2$ linker group would lead to linker groups containing double bonds. The indenes of this invention could be made by a different route, involving treatment of the proper 1-indanone with tosyl hydrazine followed by a modified Shapiro reaction with the resulting hydrazone to complete attachment of the alkoxy-substituted benzoyl moiety. An organocuprate 1,4 addition to the resultant α,β-unsaturated ketone will effect suitable attachment of the additional aryl group, while treatment with phenylselenium chloride, followed by oxidation and elimination would regenerate the indene double bond, completing the synthesis.

The ability of the various above described compounds to inhibit tubulin polymerization can be determined by in vitro assay. A suitable assay system is that described by Bai et al A method for purifying tubulin from bovine brain cells is described by Hamel and Lin. The $IC_{50}$ values for tubulin polymerization determined for some of the compounds of this invention demonstrate the importance of the alkoxy substituent at the para position of the 3-aroyl phenyl group. As described above, the $IC_{50}$ of 3-(3',4',5'-trimethoxybenzoyl)-2-(4'-methoxyphenyl)-6-methoxybenzo[b]thiophene is comparable to that of Combretastatin A-4. Otherwise identical 3,5-dimethoxybenzoyl, 2,6-dimethoxybenzoyl and 3,5-dimethoxy-4-hydroxybenzoyl compounds showed no observable tubulin polymerization inhibition activity. It is contemplated, however, that any novel benzo[b]thiophene compounds of this invention that do not inhibit tubulin polymerization may still be useful based upon their inherent estrogenicity, for example, as anti-fertility theraputics.

A measurement of each compound's tubulin affinity may also be determined through the compound's ability to inhibit colchichine-tubulin binding. A suitable assay is that described by Kang et al., involving the use of commercially available tritiated colchicine. Decreases in the amount of [$^3$H]colchicine-tubulin interaction due to the competitive binding of one of the novel inhibitors of this invention may be measured by autoradiography or scintillation counting.

The tubulin polymerization compounds can also be tested for their ability to inhibit tumor cell growth. Initially, cytotoxicity of the various compounds may be measured against the leukemia P388 cell line or other appropriate cell lines in vitro to determine which compounds will be most effective against each type of tumor cell. As in the tubulin polymerization assays, the para methoxy substituent of the 3-aroyl phenyl group was very important in producing cytotoxic activity against P388 leukemia cells. Significantly, the compounds that failed to inhibit tubulin polymerization, the 3,5-dimethoxybenzoyl, 2,6-dimethoxybenzoyl and the 3,5-dimethoxy-4-hydroxybenzoyl compounds also failed to show measurable activity against the leukemia cells. Another significant finding was that 3-(3',4',5'-trimethoxybenzoyl)-2-(4'-methoxyphenyl)-6-methoxybenzo[b]thiophene had a smaller $ED_{50}$ value than a nitrogen derivative of combretastatin, 5-[(Z)-2-(3', 4', 5'-trimethoxyphenyl)ethenyl]-2-methoxy-N,N-bis-(phenylmethyl)aniline. The in vitro activities of 3-(3',4',5'-trimethoxybenzoyl)-2-( 4'-methoxyphenyl)-6- methoxybenzo[b]thiophene against other cell lines are listed in Table 1 of Example 4 below.

As will be obvious to one of skill in the art, tubulin polymerization plays a role in diseases other than cancer. Chagas' disease, for example, is caused by *Trypanosoma cruzi*, a flagellate protozoa which has a substantial protein composition containing tubulin both as a component of the subpellicular microtubule system and the flagellum (De Souza). Chagas' disease is characterized by lesions in the heart, alimentary tract and nervous system. The disease currently affects approximately 16–18 million people and is the leading cause of myocarditis in the Americas (WHO). Inhibition of tubulin polymerization, crucial to the parasite's mobility, would provide an effective treatment. Indeed, the use of agents that selectively affect tubulin polymerization has precedence in the therapy of other parasitic diseases. The benzimidazoles are very effective anti-helmenthic drugs (Katiyar, et al.), and the dinitroanilines have shown promise against *Leishmania*, a parasite closely related to *Trypanosoma* (Chan and Gong). Currently, only two drugs exist for the treatment of Chagas' disease: benznidazole and nifurtimox. Both of these compounds are nitroheterocycles that are converted into nitro anion radicals that then interfere with macromolecular synthesis. These drugs have several adverse effects, including thrombocytopenic purpura and polyneropathy. These compounds may also cause genotoxicity in children (Marr et al., De Castro). A suitable assay for determining the tubulin polymerization inhibitors ability to treat parasites is described by Maldonado et al.

For their use in treating disease, the tubulin polymerization inhibitors may be present as part of pharmacologically active compositions suitable for the treatment of animals, particularly humans. The tubulin polymerization inhibitor or tubulin polymerization inhibitor-containing composition must then contact the tubulin-containing system wherein tubulin polymerization needs to be inhibited, for example, the tumor cells or the cells of the flagellate parasite. Pharmacologically active compositions of the tubulin polymerization inhibitors can be introduced via intravenous injection or orally in solid formulations such as tablets, chewable tablets or capsules. The preparation may also be a parenteral preparation for injection directly at the site of the tumor or parasitic infection.

The preferred dosage of the active ingredient inhibitor compound will vary depending upon the size and type of tumor or degree of parasitic infection, the patient's weight and age, and the exact identity of the tubulin polymerization inhibitor employed. The number of administrations of the pharmaceutically active composition will also vary according to the response of the individual patient to the treatment. For the treatment of cancer, suitable dosages of the tubulin polymerization inhibitors occur in amounts between 0.5 mg/kg of body weight to 100 mg/kg of body weight per day, preferably of between 1.0 mg/kg of body weight to about 20 mg/kg of body weight. It is contemplated that a similar dosage range would be suitable for the treatment of parasitic infections. Moreover, tubulin inhibition assays can also provide one of skill in the art with the appropriate concentrations of inhibitors that must reach the tubulin-containing cells, and the appropriate dosage could be calculated from that information.

The preparations of tubulin polymerization inhibitors may require the use of suitable pharmaceutically acceptable carriers. As used herein, "pharmaceutically acceptable carrier" includes any and all solvents, dispersion media, coatings, antibacterial and antifungal agents and isotonic agents and the like. The use of such media and agents for pharmaceutically active substances is well known in the art. Except insofar as any conventional media or agent is incompatible with the active ingredient, its use in the therapeutic composition is contemplated. Supplementary active ingredients can also be incorporated into the compositions. The phrase "pharmaceutically acceptable" also refers to molecular entities and compositions that do not produce an allergic or similar untoward reaction when administered to an animal or a human.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

SYNTHESIS OF THE TUBULIN POLYMERIZATION INHIBITORS

Synthesis of 3-(3',4',5'-trimethoxybenzoyl)-2-(4'-methoxyphenyl)-6-methoxy-benzo[b]thiophene 2-(4'-methoxyphenyl)-6-methoxybenzo[b]thiophene 5 was prepared according to the procedure of Kost et al. To a well-stirred solution of 5 ( 0.500 g, 1.85 mmol) and 3,4,5-trimethoxybenzoyl chloride (0.640 g, 2.77 mmol) in $CH_2Cl_2$ (20 ml), was added $AlCl_3$ (0.123 g, 0.925 mmol) portion-wise over a 15 minute period. After 5 hours (total reaction time), water was added, and the product was isolated initially by extraction with $CH_2Cl_2$ and subsequently by extraction with ethyl acetate (EtOAc). The organic layers were separately washed with brine and then combined and dried over $MgSO_4$. Purification by flash chromatography (silica gel, 60:40 EtOAc/hexane) afforded 3-(3',4',5'-trimethoxybenzoyl)-2-(4'-methoxyphenyl)-6-methoxybenzo [b]thiophene (0.537 g, 1.16 mmol, 63%) as an off-white solid. Recrystallization (hexane/ethanol) afforded a highly pure crystalline sample of the compound with mp 131°–133° C. $^1$H-NMR ($CDCl_3$, 360 Mhz): δ=7.66 (d,J=8.9 Hz, 1H, Ar$\underline{H}$)7.32 (d,J=2.4 Hz, 1H, Ar$\underline{H}$), 7.31 (d,J=8.8 Hz, 2H, Ar$\underline{H}$), 7.07 (s,2H, Ar$\underline{H}$), 7.01 (dd,J=8.9,2.4 Hz, 1H, Ar$\underline{H}$), 6.75 (d,J=8.8 Hz, 2H, Ar$\underline{H}$), 3.89 (s,3H, —OC$\underline{H}_3$), 3.83 (s,3H, —OC$\underline{H}_3$), 3.74 (s,3H, —OC$\underline{H}_3$), 3.73 (s, 6H, —OC$\underline{H}_3$); $^{13}$C-NMR ($CDCl_3$, 90 Mhz): δ=192.9, 159.9, 157.7, 152.7, 143.7, 142.6, 140.1, 133.9, 132.3, 130.3, 129.9, 126.1, 124.2, 114.9, 114.1, 107.5, 104.4, 60.8, 56.1, 55.6, 55.2 HRMS (EI) M$^+$ calcd for $C_{26}H_{24}O_6S$ 464.1294. and Anal. Calcd for $C_{26}H_{24}O_6S$: C, 67.23; H, 5.21; S, 6.90. Found: C, 67.20; H, 5.26; S, 6.88.

Synthesis of 3-(2', 6'-dimethoxybenzoyl)-2-(4'-methoxyphenyl)-6-methoxybenzo[b]thiophene To a well-stirred solution of 2-(4'-methoxyphenyl) -6-methoxybenzo[b]thiophene (0.500 g, 1.85 mmol) and 2,6-dimethoxybenzoyl chloride (1.11 g, 5.56 mmol) in $CH_2Cl_2$ (40 mL) was added $AlCl_3$ (0.986 g, 7.40 mmol) portion-wise over a 15 minute period. After 6 hours, water was added, and the product was isolated initially by extraction with $CH_2Cl_2$ and subsequently by extraction with EtOAc. The organic layers were separately washed with brine and then combined and dried over $MgSO_4$. Purification by flash chromatography (silica gel, 60:40 EtOAc/hexane) afforded the title compound (0.484 g, 1.11 mmol, 60%) as an off-white solid. Recrystallization (hexane/ethanol) afforded a highly pure, crystalline sample with mp 146°–152° C.: $^1$H-NMR (CDCl$_3$, 360 Mhz): δ=8.54 (dd,J= 9.1,0.3 Hz, 1H, ArH), 7.25 (d,J=2.1 Hz, 1H, ArH), 7.12 (d,J=8.8 Hz, 2H, ArH), 7.10 (dd,J=9.0,2.5 Hz, 1H, ArH), 6.98 (t,J=8.4 Hz, 1H, ArH), 6.58 (d,J=8.8 Hz, 2H, ArH), 6.20 (d,J=8.4 Hz, 2H, ArH), 3.88 (s,3H, —OCH$_3$), 3.73 (s,3H, —OCH$_3$), 3.60 (s,6H, —OCH$_3$); $^{13}$C-NMR (CDCl$_3$, 90 Mhz): δ=190.3, 159.5, 157.5, 157.3, 151.3, 139.3, 132.9, 131.9, 130.8, 130.5, 126.4, 125.7, 120.3 115.0, 112.6, 103.9, 103.6, 55.6, 55.5, 55.3. HRMS (EI) M$^{30}$ calcd for C$_{25}$H$_{22}$O$_5$S 434.1188, found 434.1188.

Synthesis of 3-(3–,5–-dimethoxybenzoyl)-2-(4–-methoxyphenyl)-6-methoxybenzo[b]thiophene To a well-stirred solution of 2-(4—methoxyphenyl)-6-methoxybenzo[b]thiophene (0.615 g, 2.27 mmol) and 3,5-dimethoxybenzoyl chloride (1.37 g, 6.83 mmol) in CH$_2$Cl$_2$ (45 mL) was added AlCl$_3$ (1.21 g, 9.09 mmol) portion-wise over a 15 minute period. After 17 hours, water was added, and the product was isolated initially by extraction with CH$_2$Cl$_2$ and subsequently by extraction with EtOAc. The organic layers were separately washed with brine and then combined and dried over MgSO$_4$. Purification by flash chromatography (silica gel, 60:40 EtOAc/hexane) afforded the title compound (0.475 g, 1.09 mmol, 48%) as an off-white solid. Recrystallization (hexane/ethanol) afforded a highly pure, crystalline sample with mp 114°–120° C.: $^1$H-NMR (CDCl$_3$, 360 Mhz): δ=7.59 (d,J=8.9 Hz, 1H, Ar H), 7.32 (d,J=8.5 Hz, 2H, ArH), 7.32 (d,J=2.4 Hz, 1H, Ar H), 6.98 (dd,J=9.0,2.4 Hz, 1H, ArH), 6.94 (d,J=2.1 Hz, 2H, ArH), 6.76 (d,J=8.7 Hz, 2H, ArH), 6.52 (t,J=2.4 Hz, 1H, Ar H), 3.89 (s,3H, —OCH$_3$), 3.76 (s,3H,—OCH$_3$), 3.71 (s,6H, —OCH$_3$); $^{13}$ C-NMR (CDCl$_3$, 90 Mhz): δ=194.0, 160.5, 159.8, 157.7, 143.9, 140.0, 139.3, 133.8, 130.3, 130.1, 126.0, 124.1, 114.9, 114.0, 107.6, 106.1, 104.4, 55.6, 55.5, 55.2. HRMS (EI) M$^+$ calcd for C$_{25}$H$_{22}$O$_5$S 434.1188, found 434.1245.

Synthesis of 3-(3',4'-dimethoxybenzoyl)-2-(4'-methoxyphenyl)-6-methoxybenzo[b]thiophene To a well stirred solution of 2-(4'-methoxyphenyl)-6-methoxybenzo[b]thiophene (0.327g, 1.21 mmol) and 3,4-dimethoxybenzoyl chloride (0.557 g, 2.77 mmol) in CH$_2$Cl$_2$ (20 ml) was added AlCl$_3$ (0.616 g, 4.62 mmol) portion-wise over a 15 minute period. After 7 hours, water was added, and the product was isolated initially by extraction with CH$_2$Cl$_2$ and subsequently by extraction with EtOAc. The organic layers were separately washed with brine and then combined and dried over MgSO$_4$. Purification by flash chromatography (silica gel, 60:40 Et$_2$O/hexanes) afforded the title compound (0.402 g, 0.92 mmol, 76%) as a pale yellow solid.

Synthesis of 3-(4'-methoxybenzoyl)-2-(4'-methoxyphenyl)-6-methoxybenzo[b]thiophene To a well stirred solution of 2-(4'-methoxyphenyl)-6-methoxybenzo[b]thiophene (0.305 g, 1.13 mmol) and 4-methoxybenzoyl chloride (0.378 g, 2.22 mmol) in CH$_2$Cl$_2$ (45 ml) was added AlCl$_3$ (0.550 g, 4.12 mmol) portion-wise over a 15 minute period. After 1.3 hours, water was added, and the product was isolated initially by extraction with CH$_2$Cl$_2$ and subsequently by extraction with EtOAc. The organic layers were separately washed with brine and then combined and dried over MgSO$_4$. Purification by flash chromatography (silica gel, 70:30 EtOAc/hexanes) afforded the title compound (0.3576 g, 0.88 mmol, 78%) as a pale yellow solid. Recrystallization (EtOAc/hexanes) afforded a highly pure, crystalline sample with mp 119°–120° C. $^1$H-NMR (CDCl$_3$, 360 MHz): δ=7.77 (d,J=9.0 Hz, 2H, Ar H), 7.52 (d,J=8.9 Hz, 1H, ArH), 7.35 (d,J=8.9 Hz, 2H, Ar H), 7.31 (d,J=2.3 Hz, 1H, ArH), 6.95 (dd,J=8.9,2.4 Hz, 1H, ArH), 6.76 (d,J=9.0, 2H, ArH), 6.75 (d,J=8.9,2H, ArH), 3.87 (s,3H, —OCH$_3$), 3.79 (s,3H, —OCH$_3$), 3.74 (s, 3H, —OC H$_3$); $^{13}$C-NMR (CDCl$_3$, 90 MHz): δ=193.2, 193,7, 159.7, 157.6, 142.4, 140.0, 134.0, 132.2, 130.6, 130.4, 130.2, 126.0, 124.0, 114.7, 114.0, 113.6, 104.5, 55.6, 55.4, 55.2. HRMS (EI) M$^+$ calcd for C$_{24}$H$_{20}$O$_4$S, 404.1082, found 404.1059. Anal. Calcd for C$_{24}$H$_{20}$O$_4$S: C, 71.27; H, 4.98; S, 7.93. Found: C, 71.39; H, 4.98; S, 7.90.

Synthesis of 3-(4'-ethoxybenzoyl)-2-(4'-methoxyphenyl)-6-methoxybenzo[b]thiophene To a well stirred solution of 2-(4'-methoxyphenyl)-6-methoxybenzo[b]thiophene (0.300 g, 1.11 mmol) and 4-ethoxybenzoyl chloride (0.555 g, 3.01 mmol) in CH$_2$Cl$_2$ (45 ml) was added AlCl$_3$ (0.502 g, 3.76 mmol) portion-wise over a 15 minute period. After 45 minutes, water was added, and the product was isolated initially by extraction with CH$_2$Cl$_2$ and subsequently by extraction with EtOAc. The organic layers were separately washed with brine and then combined and dried over MgSO$_4$. Purification by flash chromatography (silica gel, 70:30 EtOAc/hexanes) afforded the title compound (0.389 g, 0.93 mmol, 84%) as a white solid. Recrystallization (EtOAc/hexanes) afforded a highly pure, crystalline sample with mp 124°–125° C. $^1$H-NMR (CDCl$_3$, 360 MHz): δ=7.77 (d,J=8.9 Hz, 2H, ArH), 7.52 (d,J=8.9 Hz, 1H, 8.8 Hz, 2H, ArH), 7.31 (d,J =2.4 Hz, 1H, ArH), 6.95 (dd,J=8.9,2.4 Hz, 1H, ArH), 6.76 (d,J=8.8 Hz, 2H, ArH), 6.75 (d,J=8.9 Hz, 2H, ArH), 4.01 (q,J=7.0 Hz, 2H, CH$_2$), 3.88 (s,3H, —OCH$_3$), 3.74 (s,3H, —OCH$_3$), 1.39 (t,J=7.0, 3H, CH$_3$); $^{13}$C-NMR (CDCl$_3$, 90 Mhz): δ=193.1, 163.1, 159.7, 157.6, 142.3, 140.0, 134.0, 132.3, 130.6, 130.2, 126, 124.0, 114.7, 114.0, 114.0, 104.3, 63.7, 55.6, 55.2, 14.6. HRMS (EI) M$^+$ calcd for C$_{25}$H$_{22}$O$_4$S 418.1239, found 418.1241. Anal. Calcd for C$_{25}$H$_{22}$O$_4$S: C, 71.75; H, 5.30; S, 7.66. Found: C, 71.68; H, 5.30; S, 7.61.

Synthesis of 3-(3',4',5'-triethoxybenzoyl)-2-(4'-methoxyphenyl)-6-methoxybenzo[b]thiophene To a well stirred solution of 2-(4'-methoxyphenyl)-6-methoxybenzo[b]thiophene (0.501g, 1.85 mmol) and 3,4,5-triethoxybenzoyl chloride (1.00 g, 3.66 mmol) in CH$_2$Cl$_2$ (45 ml) was added AlCl$_3$ (0.870 g, 6.52 mmol) portion-wise over a 15 minute period. After 30 minutes, water was added, and the product was isolated initially by extraction with CH$_2$Cl$_2$ and subsequently by extraction with EtOAc. The organic layers were separately washed with brine and then combined and dried over MgSO$_4$. Purification by flash chromatography (silica gel, 70:30 EtOAc/hexanes) afforded the title compound (0.827 g, 1.63 mmol, 88%) as a pale yellow solid. Recrystallization (EtOAc/hexanes) afforded a highly pure, crystalline sample with mp 108°–110° C. $^1$H-NMR (CDCl$_3$, 360 Mhz): δ=7.64 (d,J=8.9 Hz, 1H, Ar H), 7.32 (d,J=2.3 Hz, 1H, ArH), 7.29 (d,J=8.7 Hz, 2H, Ar H), 7.02(s,2H, ArH), 6.99 (dd,J=9.0,2.4 Hz, 1H, ArH), 6.73 (d,J=8.7 Hz, 1H, ArH), 4.06 (q,J=7.1 Hz, 2H, CH$_2$), 3.91 (q,J=7.0, 4H, CH$_2$), 3.89 (s,3H, —OCH$_3$), 3.74 (s,3H, —OC H$_3$), 1.34 (t,J=7.0 Hz, 6H, CH$_3$), 1.28 (t,J=7.1 Hz, 3H, C H$_3$; $^{13}$C-NMR (CDCl$_3$, 90 MHz): δ=193.2 , 159.8, 157.7, 152.5, 143.6, 142.6, 140.0, 133.9, 132.3, 130.3, 130.1, 126.0, 124.2, 114.8, 114.0, 108.9, 104.4, 68.8, 64.6, 55.6, 55.2, 15.4, 14.7. HRMS (EI) M+ calcd for $C_{29}H_{30}O_6S$ 506.1763, found 506.1777. Anal. Calcd for $C_{29}H_{30}O_6S$: C, 68.75; H, 5.97; S, 6.33. Found: C, 68.67; H, 5.97; S, 6.27.

Synthesis of 3-[3'(3",4",5"-trimethoxyphenyl) propionyl]-2-(4'methoxyphenyl)-6-methoxybenzo[b] thiophene To a well-stirred solution of 2-(4'-methoxyphenyl)-6-methoxybenzo[b]thiophene (0.206 g, 0.762 mmol) and 3-(3',4',5'-trimethoxyphenyl)propionyl chloride (0.390 g, 1.51 mmol) in $CH_2Cl_2$ (50 mL) was added $AlCl_3$ (0.520 g, 3.89 mmol) portion-wise over a 15 minute period. After 18 hours (total reaction time), water was added, and the product was isolated initially by extraction with $CH_2Cl_2$ and subsequently by extraction with EtOAc. The organic layers were separately washed sequentially with $NaHCO_3$ (sat) and brine and then combined and dried over $MgSO_4$. Purification by flash chromatography (silica gel, 70:30 EtOAc/hexane) afforded the title compound as an off-white solid. $^1$H-NMR (CDCl$_3$, 360 Mhz): δ=7.92 (d,J=8.9 Hz, 1H, ArH), 7.35 (d,J=8.7 Hz, 2H, ArH), 7.25 (m,1H, ArH), 7.04 (dd,J=8.9,2.4 Hz, 1H, ArH), 6.93 (d,J=8.7 Hz, 2H, ArH), 6.15 (s,2H, Ar H) 3.88 (s,3H, —OCH$_3$), 3.85 ((s,3H, —OCH$_3$), 3.78 (s, 3H, —OCH$_3$), 3.72 (s,6H, —OCH$_3$), 3.80 (t,2H, CH$_2$), 3.70 (t,2H, CH$_2$).

EXAMPLE 2

TUBULIN POLYMERIZATION ASSAY $IC_{50}$ values for tubulin polymerization were determined according to the procedure described in Bai et al. Purified tubulin is obtained from bovine brain cells as described in Hamel and Lin. Various amounts of inhibitor were preincubated for 15 minutes at 37° C. with purified tubulin. After the incubation period, the reaction was cooled and GTP was added to induce tubulin polymerization. Polymerization was then monitored in a Gilford spectrophotometer at 350 nm. The final reaction mixtures (0.25 ml) contained 1.5 mg/ml tubulin, 0.6 mg/ml microtubule-associated proteins (MAPs), 0.5 mM GTP, 0.5 mM $MgCl_2$, 4% DMSO and 0.1M 4-morpholineethanesulfonate buffer (MES, pH 6.4). $IC_{50}$ is the amount of inhibitor needed to inhibit tubulin polymerization 50% with respect to the amount of inhibition that occurs in the absence of inhibitor. The $IC_{50}$ value determined for 3-(3',4',5'-Trimethoxybenzoyl)-2-(4'-methoxyphenyl)-6-methoxybenzo[b]thiophene was 1.5 –2.5 μM.

EXAMPLE 3

CYTOTOXIC ASSAY WITH P388 LEUKEMIA CELLS

Some of the newly prepared compounds were evaluated for cytotoxic activity against P388 leukemia cells using an assay system similar to the National Institutes of Cancer procedure described below and in Monks et al. The $ED_{50}$ value (defined as the effective dosage required to inhibit 50% of cell growth) of 3-(3',4',5'-trimethoxybenzoyl)-2-(4'-methoxyphenyl)-6-methoxybenzo[b]thiophene was found to by 22.2 μg/ml. The $ED_{50}$ values of 3,5-dimethoxybenzoyl, 2,6-dimethoxybenzoyl and 3,5-dimethoxy-4-hydroxybenzoyl derivatives of 2-(4-methoxyphenyl)-6-methoxybenzo[b]thiophene compounds were estimated as greater than 100 μg/ml. The $ED_{50}$ value of a nitrogen derivative of combretastatin, 5-[(Z)-2-(3',4',5'-trimethoxyphenyl)ethenyl]-2-methoxy-N,N-bis-(phenylmethyl)aniline was 33.9 μg/ml.

EXAMPLE 4

GROWTH INHIBITORY ACTIVITY AGAINST OTHER CANCER CELL LINES 3-(3',4',5'-Trimethoxybenzoyl)-2-(4'-methoxyphenyl)-6-methoxybenzo[b]thiophene was evaluated in terms of growth inhibitory activity against several human cancer cell lines, including ovarian CNS, renal, lung, colon and melanoma lines. The assay used is described in Monks et al. Briefly, the cell suspensions, diluted according to the particular cell type and the expected target cell density (5,000–40,000 cells per well based on cell growth characteristics), were added by pipet (100 μl) to 96-well microtiter plates. Inoculates were allowed a preincubation time of 24–28 hours at 37° C. for stabilization. Incubation with the inhibitor compounds lasted for 48 hours in 5% $CO_2$ atmosphere and 100% humidity. Determination of cell growth was done by in situ fixation of cells, followed by staining with a protein-binding dye, sulforhodamine B (SRB), which binds to the basic amino acids of cellular macromolecules. The solubilized stain was measured spectrophotometrically. The results of these assays are shown in Table 1. $GI_{50}$ is defined as the dosage required to inhibit tumor cell growth by 50%.

TABLE 1

Activity of 3-(3',4',5'-Trimethoxyphenyl)-2-(4'-methoxyphenyl)-6-methoxybenzo[b]thiophene Against Human Cancer Cell Lines.

| Cell Type | Cell-Line | $GI_{50}$ (μg/ml) |
|---|---|---|
| Ovarian | OVCAR-3 | $1.9 \times 10^{-1}$ |
| CNS | SF-295 | $2.0 \times 10^{-1}$ |
| Renal | A498 | $4.6 \times 10^{-1}$ |
| Lung-NSC | NCI-H460 | $1.3 \times 10^{-1}$ |
| Colon | KM20L2 | $4.9 \times 10^{-2}$ |
| Melanoma | SK-MEL-5 | $4.8 \times 10^{-1}$ |

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Bai, Schwartz, Kepler, Pettit and Hamel, "Characterization of the Interaction of Cryptophycin 1 with Tubulin: Binding in the Vinca Domain, Competitive Inhibition of Dolastatin 10 Binding and an Unusual Aggregation Reaction," Cancer Res., 56:4398–4406, 1996.

Black and Clemens, U.S. Pat. No. 4,656,187.

Boger and Curran, "Synthesis of the lower subunit of rhizoxin," *J. Org. Chem.*, 57:2235, 1992.

Cameron, Da Silva-Jardine, Larson, Hauske, Rosati, WO 95/10513.

Carlson, Cullinan, Fahey, Jackson, Roehm, Spaethe, U.S. Pat. No. 5,532,382.

Chan and Gong, "Inhibition of Leishmanias but not host macrophages by the antitubulin herbicide Trifluralin," *Science*, 249:924–926, 1990.

Chavan, Richardson, Kim, Haley, Watt, Forskolin, "Photoaffinity probes for the evaluation of tubulin binding sites," *Bioconjugate Chem.*, 4:268, 1993.

Cushman, Nagarathnam, Gopal, Chakraborti, Lin, Hamel, "Synthesis and evaluation of stilbene and dihydrostilbene derivatives as potential anticancer agents that inhibit tubulin polymerization," *J. Med. Chem.*, 34:2579, 1991.

D'Amato, Lin, Flynn, Folkman, Hamel, "2-methoxyesteradiol, an endogenous mammalian metabolite, inhibits tubulin polymerization by interacting at the colchicine site," *Proc. Natl. Acad. Sci. USA*, 91:3964, 1994.

De Castro, "The challenge of Chagas' disease chemotherapy: an update of drugs assayed against *Trypanasoma cruzi*," Acta. Trop., 53:83–98, 1993.

De Souza, "Cell biology of *Trypanasoma cruzi*," *Internat. Rev. Cytol*, 86:197–275, 1984.

Eaton, Gold, Zichi, "Let's get specific: the relationship between specificity and affinity," *Chemistry and Biology*, 2: 633–638, 1995.

Floyd, Barnes, Williams, "Photoaffinity labeling of tubulin with (2-nitro-4-azidophenyl)deacetylcolchicine: direct evidence for two colchicine binding sites," *Biochemistry*, 28:8515, 1989.

Gerwick, Proteau, Nagle, Hamel, Blokhin, Slate, "Structure of curacin A, a novel antimitotic, antiproliferative, and brine shrimp toxic natural product from the marine cyanobacterium *Lyngbya majuscula*," *J. Org. Chem.*, 59:1243, 1994.

Hahn, Hastie, Sundberg, "Synthesis and evaluation of 2-diazo-3,3,3-trifluoropropanoyl derivatives of colchicine and podophyllotoxin as photoaffinity labels: reactivity, photochemistry, and tubulin binding, " *Photochem. Photobiol*, 55:17, 1992.

Hamel and Lin, "Separation of active tubulin and microtubule-associated proteins by ultracentrifugation and isolation of a component causing the formation of microtubule bundles," *Biochemistry*, 23:4173, 1984.

Jiang, Hesson, Dusak, Dexter, Kang, Hamel, "Synthesis and biological evaluation of 2-styrylquinazoline-4(3H)-ones, a new class of antimitotic anticancer agents which inhibit tubulin polymerization," *J. Med. Chem.*, 33:1721, 1990.

Jones, Jevnikar, Pike, Peters, Black, Thompson, Falcone, Clemens, "Antiestrogens. 2. Structure-activity studies in a series of 3-aroyl-2-arylbenzo[b]thiophene derivatives leading to [6-hydroxy-2-(4-hydroxyphenyl)benzo[b]thien-3-yl][4-[2(1-piperidinyl)ethoxy]phenyl]metahanone hydrochloride (LY156758), a remarkably effective estrogen antagonist with only minimal intrinsic estrogenicity," *J. Med. Chem.*, 27:1057, 1984.

Jones and Suarez, U.S. Pat. No. 4,133,814.

Jones, Suarez, Massey, Black, Tinsley, "Synthesis and antiestrogenic activity of [3,4-dihydro-2-(4-methoxyphenyl)-1-naphthalenyl][4 -[2-(1-pyrrolidinyl)ethoxy]-phenyl]methanone, methanesulfonic acid salt," *J. Med. Chem.*, 22:962, 1979.

Kang, Getohun, Muzaffar, Brossi, Hamel, "N-acetylcolchinol O-methyl ether and triocolchicine, potent analogs of colchicine modified in the C ring," *J. Biol. Chem.*, 265, 10255, 1990.

Katiyar, Gordon, McLaughlin, Edlind, "Antiprotozoal activities of benzimidazoles and correlations with β-tubulin sequence," *Antimicrob. Agents Chemother.*, 38:2086–2090, 1994.

Kingston, Samaranayake, Ivey, "The chemistry of taxol, a clinically useful anticancer agent," *J. Nat. Prod.*, 53:1, 1990.

Kobayashi, Nakada, Ohno, "Synthetic study on an antitumor antibiotic rhizoxin by using an enzymatic process on prochiral beta-substituted glutarates," *Pure Appl. Chem.*, 64:1121, 1992.

Kobayashi, Nakada, Ohno, "Synthetic study on an antitumor antibiotic rhizoxin by using an enzymatic process on prochiral beta-substituted glutarates," *Indian J. Chem.*, 32B:159, 1993.

Kost, Budylin, Matveeva and Sterligov, *Zh. Org Khim*, 6:1503, 1970.

Kym, Anstead, Pinney, Wilson, Katzenellenbogen, "Molecular structures, conformational analysis, and preferential modes of binding of 3-aroyl-2-arylbenzol[b]thiophene estrogen receptor ligands: LY117018 and aryl azide photoaffinity labeling analogs," *J. Med. Chem.*, 36:3910, 1993.

Laitman, "Acute Chagas disease via blood transfuions," *TDR News*, 30:5, 1989.

Lavielle, Havtefaye, Schaeffer, Boutin, Cudennec, Pierre, "New α-amino phosphonic acid derivatives of vinblastine: chemistry and antitumor activity," *J. Med. Chem.*, 34:1998, 1991.

Lin, Ho, Pettit, Hamel, "Antimitotic natural products combretastatin A-4 and combretastatin A-2: studies on the mechanism of their inhibition of the binding of colchicine to tubulin," *Biochemistry*, 28:6984, 1989.

Marr and Docamp, "Chemotherapy for Chagas' disease: A perspective of current therapy and considerations for future research," *Rev. Infect. Dis.*, 8:884–903, 1986.

Mouridsen, Palshof, Patterson and Battersby, *Cancer Treat. Rev.*, 5:131, 1978.

Monks, Scudiero, Skehan, Shoemaker, Pauli, Vistica, Hose, Langley, Cronise, Vaigro-Wolff, Gray-Goodrich, Campbell, Mayo, and Boyd, "Feasibility of a high-flux anti-cancer drug screen using a diverse panel of cultered human tumor cell lines," *J. Nat. Cancer Inst.*, 83:757–766, 1991.

Maldonado, Molina, Payeres and Urbina, "Experimental Chemotherapy with Combinations of Ergosterol Biosynthesis Inhibitors in Murine Models of Chagas' Disease," Antimicrobial Agents and Chemotherapy, 37:1353–1359, 1993.

Mullica, Pinney, Dingeman, Bounds, Sappenfield, "X-ray structures of two methoxybenzol[b]thiophenes," *J. Chem. Cryst.*, accepted for publiccation.

Muzaffar, Brossi, Lin, Hamel, "Antitubulin effects of derivatives of 3-demethylthiocolchicine, methylthio ethers of natural colchicinoids, and thioketones derived from thiocolchicine. Comparison with colchicinoids," *J. Med. Chem.*, 33:567, 1990.

Nakada, Kobayashi, Iwasaki, Ohno, "The first total synthesis of the antitumor macrolide rhizoxin: synthesis of the key building blocks," *Tetrahedron Lett.*, 34:1035, 1993.

Nakada, Kobayashi, Iwasaki, Ohno, "The first total synthesis of the antitumor macrolide rhizoxin," *Tetrahedron Lett.*, 34:1039, 1993.

Owellen, Hartke, Kickerson, Hains, "Inhibition of tubulin-microtubule polymerization by drugs of the vinca alkaloid class," *Cancer Res.*, 36:1499, 1976.

Parness and Horwitz, "Taxol binds to polymerized tubulin in vitro," *J. Cell Biol.*, 91:479, 1981.

Pettit, Cragg, Herald, Schmidt, Lohavanijaya, "Isolation and structure of combretastatin," *Can. J. Chem.*, 60:1374, 1982.

Pettit, Cragg, Singh, "Antineoplastic agents,122. constituents of combretum caffrum," *J. Nat. Prod.*, 50:386, 1987.

Pettit, Singh, Cragg, "Synthesis of natural (−)-combretastatin," *J. Org. Chem.,* 50:3404, 1985.

Pinney and Katzenellenbogen, "Synthesis of tetrafluor-substituted aryl azide and its protio analogue as photoaffinity labeling reagents for the estrogen receptor," *J. Org. Chem.,* 56:3125, 1991.

Pinney, Carlson, Katzenellenbogen, Katzenellenbogen, "Efficient and selective photoaffinity labeling of the estrogen receptor using two nonsteroidal ligands that embody aryl azide or tetrafluoroaryl azide photoreactive functions," *Biochemistry,* 30:2421, 1991.

Prata, "Chagas' Disease," *Infect. Dis. Clin. North. Amer.,* 8:61–76, 1994.

Rao, Bhanu, Sharma, "Studies directed towards the total synthesis of rhizoxin: stereoselective synthesis of C-12 to C-18 segment," *Tetrahedron Lett.* 34:707, 1993.

Rao, Horwitz, Ringel, "Direct photoaffinity labeling of tubulin with taxol," *J. Natl. Cancer Inst.,* 84:785, 1992.

Rao, Krauss, Heerding, Swindell, Ringel, Orr, Horwitz, "3'-(p-azidobenzamido)taxol photolabels the N-terminal 31 amino acids of β-tubulin," *J. Biol. Chem.,* 269:3132, 1994.

Rao, Sharma, Bhanu, "Radical mediated enantioselective construction of C-1 to C-9 segment of shizoxin," *Tetrahedron Lett.* 33:3907, 1992.

Safa, Hamel, Felsted, "Photoaffinity labeling of tubulin subunits with a photoactive analog of vinblastine," *Biochemistry,* 26:97, 1987.

Sawada, Hashimoto, Li, Kobayashi, Iwasaki, "Fluorescent and photoaffinity labeling derivatives of rhizoxin, " *Biochem. Biophys. Res. Commun.,* 178:558, 1991.

Sawada, Kato, Kobayashi, Hashimoto, Watanabe, Sugiyama, Iwasaki, "A fluorescent probe and a photoaffinity labeling reagent to study the binding site of maytansine and rhizoxin on tubulin," *Bioconjugate Chem.,* 4:284, 1993.

Sawada, Kobayashi, Hashimoto, Iwasaki, "Identification of the fragment photoaffinity-labeled with azidodansyl-rhizoxin as Met-363—Lys-379 on beta-tubulin," *Biochem Pharmacol.,* 45:1387, 1993.

Schiff, Fant, Horwitz, "Promotion of microtubule assembly in vitro by taxol, " *Nature,* 277:665, 1979.

Shirai, Tokuda, Koiso, Iwasaki, "Synthesis and anti-tubulin activity of aza-combretastatins," *Biomedical Chem. Lett.,* 699, 1994.

Staretz and Hastie, "Synthesis, photochemical reactions, and tubulin binding of novel photoaffinity labeling derivatives of colchicine," *J. Org. Chem.,* 58:1589, 1993.

Swindell, Heerding, Krauss, Horwitz, Rao, Ringel, "Characterization of two taxol photoaffinity analogues bearing azide and benzophenone-related photoreactive substituents in the A-ring side chain," *J. Med. Chem.,* 37:1446, 1994.

Swindell, Krauss, Horwitz, Ringel, "Biologically active taxol analogs with deleted A-ring side chain substituents and variable C-2' configurations," *J. Med. Chem.,* 34:1176, 1991.

Williams, Mumford, Williams, Floyd, Aivaliotis, Martinez, Robinson, Barnes, "A photoaffinity derivative of colchicine: 6-(4'-axido-2'-nitrophenylamino)hexanoyldeacetylcolchicine, photolabeling and location of the colchicine-binding site on the alpha-subunit of tubulin," *J. Biol. Chem.,* 260:13794, 1985.

Wolff, Knipling, Cahnmann, Palumbo, "Direct photoaffinity labeling of tubulin with colchicine," *Proc. Natl. Acad. Sci. USA,* 88:2820, 1991.

World Health Organization, Tropical disease research progress, 1991–1992.

What is claimed is:

1. A method for inhibiting in vitro growth of tumor cells by contacting said cells with an effective tubulin polymerization inhibiting amount of a compound of the structure:

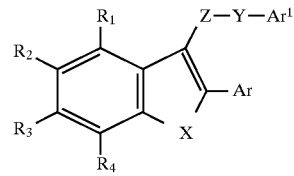

wherein

X is S, $R_1$–$R_4$ are independently chosen from the group consisting of H, OH and $C_1$–$C_5$ alkoxy, Z is chosen from the group consisting of C=O, $CH_2$, $C_2H_2$, CHOH, and $CHOCH_3$, Y is chosen from the group consisting of a covalent bond, $CH_2$, and $CH_2CH_2$, and Ar and Ar' are aryl substituents chosen from the group consisting of phenyl and naphthyl, further substituted with at least one $C_1$–$C_5$ alkoxy group.

2. The method of claim 1 wherein said tumor cells are human ovarian, CNS, renal, lung-NSC, colon or melanoma cells.

3. The method of claim 1 wherein said compound is 3-(3',4',5'-trimethoxybenzoyl)-2-(4'-methoxyphenyl)-6-methoxybenzo[b]thiophene.

4. The method of claim 1 wherein the effective amount of the compound is a between 0.5 μM and 10 μM.

5. The method of claim 1 wherein the effective amount of the compound is between 2 μM and 6 μM.

6. The method of claim 1 wherein Z is C=O.

7. The method of claim 1 wherein Ar' is chosen from the group consisting of 3,4,5-trimethoxyphenyl, 3,4-dimethoxyphenyl, 4-methoxyphenyl, 4-ethoxyphenyl, 3,4-diethoxyphenyl and 3,4,5-triethoxyphenyl.

8. The method of claim 1 wherein Ar is 4-methoxyphenyl.

9. The method of claim 1 wherein said compound is selected from the group containing [3-(3',4'-dimethoxybenzoyl)-2-(4'-methoxyphenyl)-6-methoxybenzo [b]thiophene, 3-(4'-ethoxy-benzoyl)-2-(4'-methoxyphenyl)-6-methoxybenzo[b]thiophene, 3-(3',4',5'-triethoxy-benzoyl)-2-(4'-methoxyphenyl)-6-methoxybenzo[b]thiophene, and 3-[3'-(3",4",5"-trimethoxyphenyl)propanoyl]-2-(4'methoxyphenyl)-6-methoxybenzo[b]thiophene] 3-(3',4'-dimethoxybenzoyl)-2-(4'-methoxyphenyl)-6-methoxybenzo{b}thiophene, 3-(4'-ethoxy-benzoyl)-2-(4'-methoxyphenyl)-6-methoxybenzo{b}]thiophene, 3-(3',4',5'-triethoxy-benzoyl)-2-(4'-methoxyphenyl)-6-methoxybenzo{b}-thiophene, and 3-{3'-(3",4",5"-trimethoxyphenyl)propanoyl}-2-(4'methoxyphenyl)-6-methoxybenzo{b}thiophene.

10. The method of claim 1 wherein said compound is [3-(3',4',5'-trimethoxybenzoyl)-2-(4'-methoxyphenyl)-6-methoxybenzo[b]thiophene] 3-(3',4',5'-trimethoxybenzoyl)-2-(4'-methoxyphenyl)-6-methoxybenzo{b}thiophene.

11. The method of claim 1 wherein said compound is [3-(4'-methoxybenzoyl)-2-(4-methoxyphenyl)-6-methoxybenzo[b]thiophene] 3-(4'-methoxybenzoyl)-2-(4-methoxyphenyl)-6-methoxybenzo{b}thiophene.

* * * * *